United States Patent
Greer, Jr. et al.

(10) Patent No.: US 6,393,736 B1
(45) Date of Patent: May 28, 2002

(54) ADJUSTABLE BRACE ORTHOTIC AND METHOD OF TREATING PLANTAR FASCIITIS AND RELATED FOOT DISORDERS

(75) Inventors: Jack K. Greer, Jr., Oak Ridge; W. Gilmer Reed, Jr., Strawberry Plains; John C. McCracken, Knoxville, all of TN (US)

(73) Assignee: Greer Reed Biomedical, LLC, Oak Ridge, TN (US)

( * ) Notice: Subject to any disclaimer, the term of this patent is extended or adjusted under 35 U.S.C. 154(b) by 0 days.

(21) Appl. No.: 09/723,063

(22) Filed: Nov. 27, 2000

Related U.S. Application Data

(63) Continuation-in-part of application No. 09/578,653, filed on May 25, 2000.

(51) Int. Cl.[7] .................................................. A61F 5/14
(52) U.S. Cl. ............................ 36/155; 36/145; 36/161; 36/91; 36/156
(58) Field of Search ............................ 36/91, 145, 150, 36/155–162, 166, 173, 147, 174, 180, 182, 88; 12/146 M, 142 N

(56) References Cited

U.S. PATENT DOCUMENTS

| | | | | |
|---|---|---|---|---|
| 717,523 A | * | 1/1903 | Arrowsmith | 36/166 |
| 815,897 A | * | 3/1906 | Arrowsmith | 36/173 |
| 899,367 A | * | 9/1908 | Winchell | 36/156 |
| 909,858 A | * | 1/1909 | Apgar | 36/161 |
| 1,289,738 A | * | 12/1918 | Gulick | 36/156 |
| 1,311,240 A | * | 7/1919 | Mayer | 36/157 |
| 2,022,247 A | * | 11/1935 | Lobel | 36/168 |
| 2,075,942 A | * | 4/1937 | Howell | 36/161 |
| 2,779,110 A | * | 1/1957 | Howell | 36/156 |

* cited by examiner

Primary Examiner—Mickey Yu
Assistant Examiner—Jila M. Mohandesi
(74) Attorney, Agent, or Firm—Jack K. Greer, Jr.

(57) ABSTRACT

An arch brace orthotic includes an adjustable arch curve having a plurality of extensions separated by incisions which separate the arch curve surface into multiple resiliently cantilevered extensions. The extensions adjust the arch curve height and slopes during each foot-strike along the arch curve. The weighted arch curve height is returned to an unweighted height by flexibly rebounding of each extension to support the arch of the user's foot. A tensioning means is connectable under the arch brace, providing adjustment of the arch curve height and slope to therapeutically support the user's arch. The arch brace is movable without disassembly between any shoe for treatment of arch and foot disorders. A method of treating plantar fasciitis and related foot disorders includes selectively and periodically adjusting the arch curve height and slopes by manipulating the tensioning means for therapeutic support and user controlled strengthening of the user's arch and foot.

11 Claims, 3 Drawing Sheets

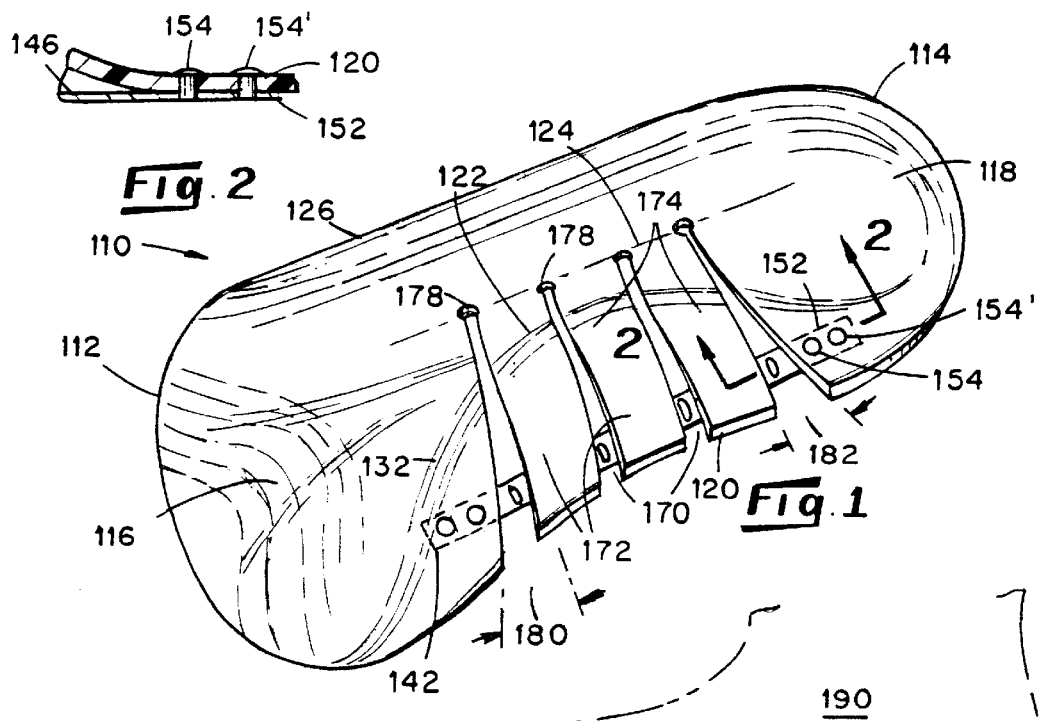
Fig. 2
Fig. 1
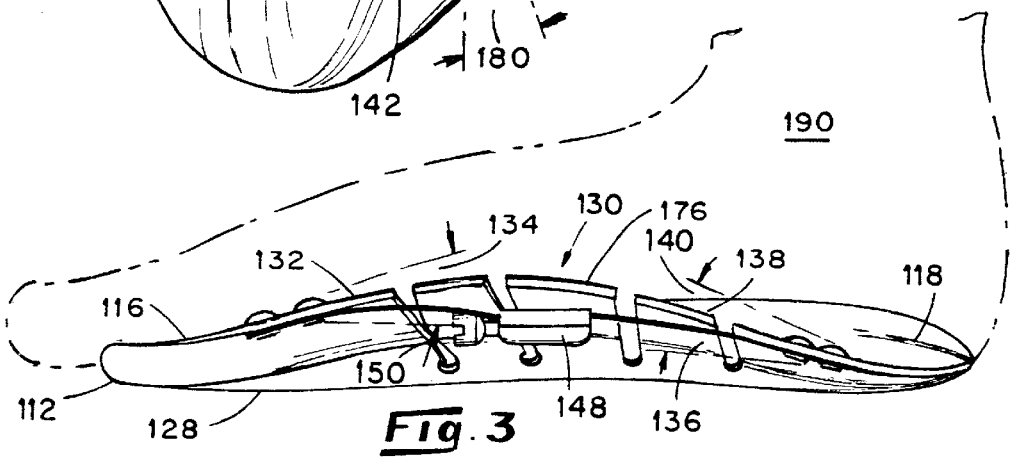
Fig. 3
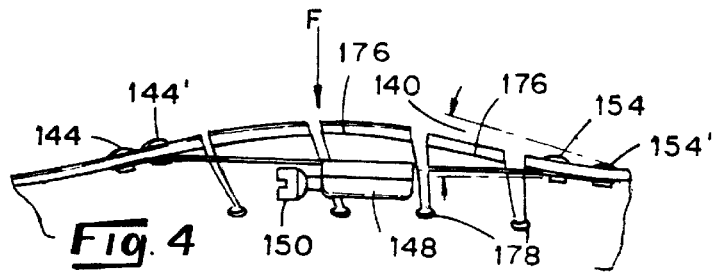
Fig. 4
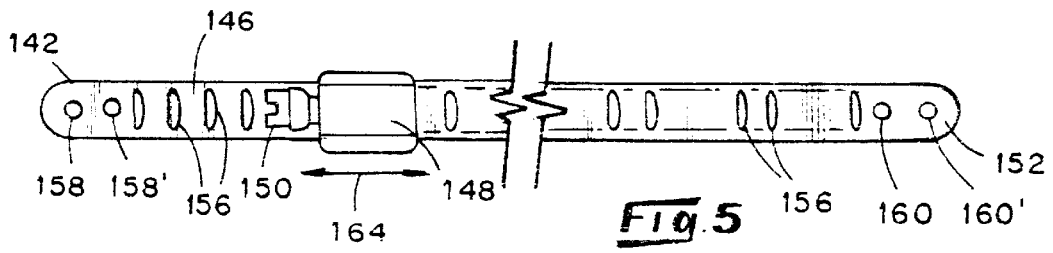
Fig. 5

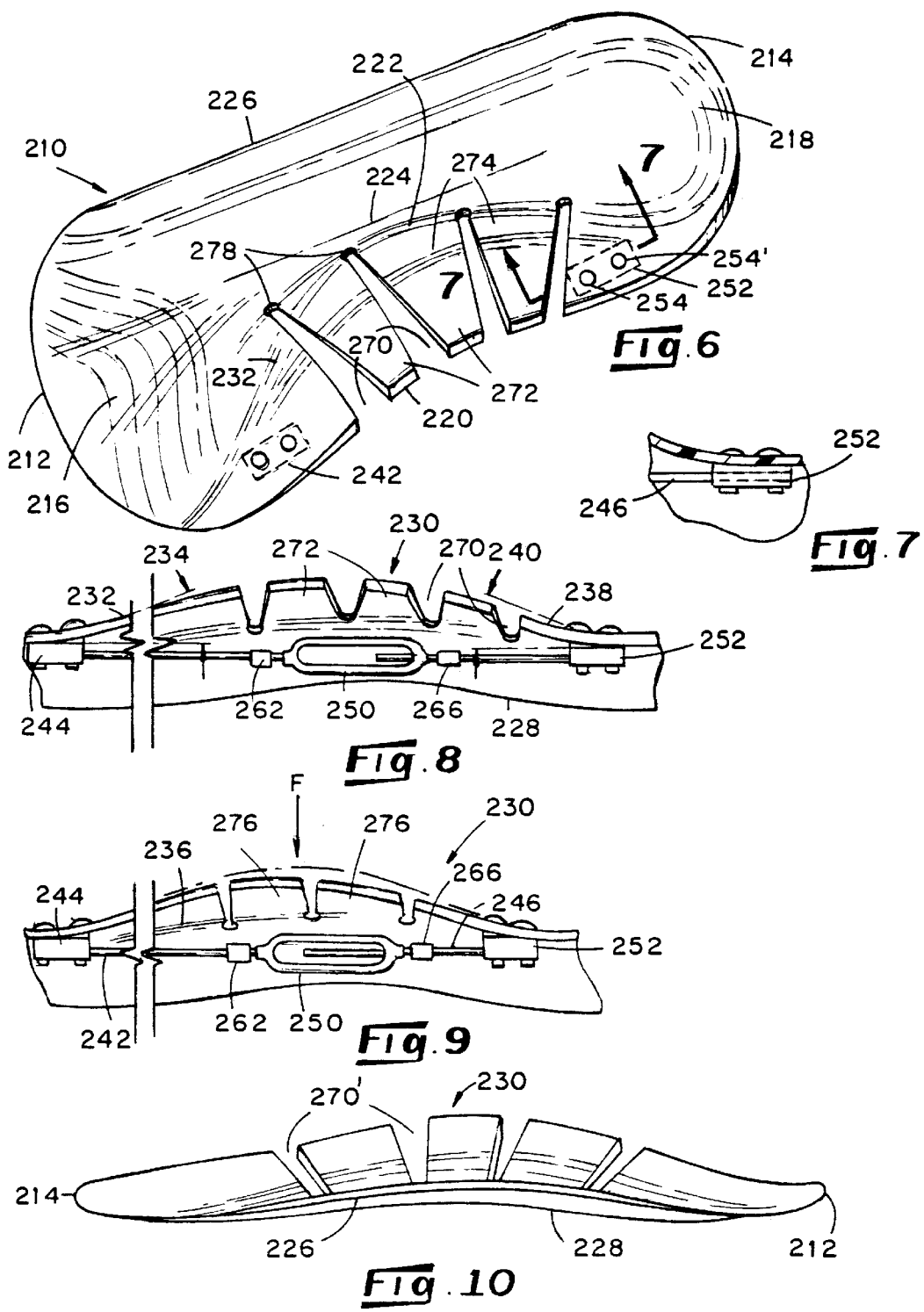

ADJUSTABLE BRACE ORTHOTIC AND METHOD OF TREATING PLANTAR FASCIITIS AND RELATED FOOT DISORDERS

CROSS-REFERENCE TO RELATED APPLICATIONS

This continuation-in-part patent application discloses and claims subject matter disclosed in the copending U.S. patent application Ser. No. 09/578,653, filed on May 25, 2000, entitled "Orthotic Arch Support Including Self-Adjusting Arch Curve And Method Of Using Orthotic."

STATEMENT REGARDING FEDERALLY SPONSORED RESEARCH OR DEVELOPMENT

Not Applicable.

BACKGROUND OF INVENTION

1. Field of Invention

This invention relates generally to the field of arch support orthosis for feet, and more particularly to a therapeutic arch brace orthosis having an adjustable arch curve and a method of treating foot disorders.

2. Description of Related Art

Prior arch support orthotics provide flexible cushioning material for support of an arch of a foot. Typical prior art insole supports have provided pliable cushion pads that can be utilized to build up the cushioning materials of a shoe insole for support of an arch. An adjustable arch support is described in U.S. Pat. No. 5,903,985, issued to DeMarchi, which discloses a sport boot that contains a supporting structure that includes a flexible, elastically deformable element having support blades attached within the sport boot. A central support blade is adjustable laterally with an externally accessed control bolt built into the exterior base of the sport boot. The support blades are required to be installed as a single unit into a specially designed sport boot having the required externally accessed control bolt, and therefore is not transferable to other shoes.

U.S. Pat. No. 5,611,153, issued to Fisher et al., discloses an insole for relieving bottom of heel pain by providing a pliable contoured insole with upwardly curved pliable arch and a depression for the heel of the foot. The arch has a non-adjustable height.

U.S. Pat. No. 5,400,528, issued to Skinner et al., discloses a cushion insole including a separate pliable arch support member which can be replaced as a unit with similar arch support members of various sizes to conform to the arch of the user. The arch support member can be moved forward or backwards if removed from the shoe and must be replaced as a unit when the pliable insole is removed from the shoe of the user.

U.S. Pat. No. 4,813,157, issued to Boisvert, et al., discloses an adjustable shoe insole having superimposed layers of flexible pad materials such as leather and/or cork that are stacked for height adjustment of the arch support. The height of the arch area is adjusted by adding or removing multiple flexible pad materials if the insole is removed from the shoe and the foot is not contacting the insole.

U.S. Pat. No. 4,166,329, issued to Herbig, discloses an adjustable arch support having a stiff, formed arch support and a metal adjusting lever that is adjustable horizontally with an external adjusting bolt. The arch support and adjusting lever are only moved as a connected unit and the longitudinal curvature of the arch curve is not altered during horizontal movement of the adjusting lever. The arch support must be utilized in a specially designed shoe as a unit and requires a hollow area in the shoe insole and sole to accommodate the external adjusting bolt which is turned by an external adjusting tool.

The prior arch supports only provide arch adjustments that are generally lateral movements of stackable members or lateral movements of support members controlled by adjusting bolts that are external to the shoe and that require significant modifications to enclosing shoes or sports boots. Therefore, there is a need for an improved adjustable arch support brace providing therapeutic support of the longitudinal arch of a foot, with the medial longitudinal arch curve of the arch support brace being intrinsically self-adjusting in height during each weighted and unweighted repetitive cycle of walking and/or running. There is an additional need for providing a method of treatment of foot disorders using an arch brace having an adjustable medial longitudinal arch curvature that is selectively adjustable in arch curve height, and adjustable in forward slope and rear slope of the arch curve by the user of the arch support brace for treatment of heel spurs, plantar fasciitis, arch pain, tendinitis, metatarsalgia, and/or related foot disorders. An additional need is to provide an arch brace having repetitively adjusting height and slope of the medial longitudinal arch curve, with the height and slope of the arch curve being extrinsically adjustable by user manipulation of a tensioning means connecting to the underside of the arch curve for therapeutic and progressive strengthening of the arch and foot to prevent recurrence of arch and foot pain.

Therefore, it is an object of the present invention to provide an adjustable arch brace for therapeutic support of the arch of the foot of a user.

It is a further object of the present invention to provide an adjustable arch curve brace for therapeutic support of the arch of the foot and that is removably insertable in any appropriately sized shoe, boot, sandal, and/or foot support cast of a user.

It is a further object of the present invention to provide an arch curve brace having a repetitively adjustable arch curve height and slope.

It is a further object of the present invention to provide an adjustable arch brace providing generally rigid support for the forefoot and heel areas of the foot, and providing adjustable anterior and posterior slopes of the arch curve of the brace.

It is a further object of the present invention to provide an adjustable arch brace having a medial longitudinal arch curvature that adjusts in height to support the arch of the foot with each step taken by the wearer of the arch brace.

It is a further object of the present invention to provide an adjustable arch support brace having an adjustable arch curve that is selectively adjustable in height and slope by the user without the direct supervision of a physician.

It is a further object of the present invention to provide a method of utilizing an adjustable arch brace having an adjustable arch curve that supports the arch of the foot to prevent the arch from moving downward excessively during each stride by the user.

It is a further object of the present invention to provide a method of treatment of inflamation and pain in the feet by applying an adjustable arch brace having an adjustable arch curve that is selectively adjustable in height and slope by the user of the arch brace when worn against the foot or feet of the user.

BRIEF SUMMARY OF INVENTION

The invention comprises an arch support brace having an adjustable arch curve, the arch support brace being positionable underneath the foot and being sized and shaped to be removably placed in a shoe or other foot enclosure worn by a user. The arch support brace includes an orthosis sized for support of the plurality of contours of the underside of the foot from about the metatarsal bones of the forefoot portion, to about the calcaneus bone of the heel portion, and includes an interior side and an outer lateral side. An arch support curve of the upper surface of the orthosis includes a medial longitudinal arch surface along the interior side, and including an anterior slope that is inclined at the leading portion of the arch curve toward the forefoot portion, a posterior slope that is inclined at the trailing portion of the arch curve toward the heel portion, and a medial slope that is inclined from the medial longitudinal arch surface toward the outer lateral side of the orthosis.

The arch support brace includes a plurality of extensions along the medial longitudinal arch surface, with the extensions being separated by a plurality of incisions along an upper surface of the arch support curve. Each incision originates along the interior side and each separately extends along each of the anterior slope, the posterior slope, and along the medial slope, therefore separating the upper surface of the arch curve into a plurality of cantilevered extensions being maintained at a neutral height along the arch support curve when in an unweighted position.

During each foot-strike, the extensions are forced downward depending on the rigidity of each extension base, the flexibility of each cantilevered extension, and the force imposed onto the arch curve, thereby collapsing the height of the arch curve until the width between each extension is diminished. Each of the extensions flexibly rebounds to an unweighted position when the force is transferred off of the arch curve. Therefore, the self-adjustable upper surface of the arch curve flexibly supports a user's arch during unweighted use, as when sitting, and supports the user's arch at a compressed arch curve height during each foot-strike, providing continuous and therapeutic support of the user's arch. Therapeutic support of the user's arch by the weighted, compressed arch curve limits the overall flattening of the user's arch during each foot-strike while wearing the arch support brace. The arch curve posterior slope is inclined at about an angle of declination towards the heel, maintaining an angle of declination for therapeutic support of the arch along the portion that the plantar fascia is connected to the calcaneus bone.

A means of tensioning is connectable under the arch curve, and includes an adjusting means attached thereon. The tensioning means and adjusting means allows the user to adjust the tensioning means, thereby adjusting the anterior angle of the anterior slope, the posterior angle of the posterior slope, and adjusting the height of the arch curve and the tension of the extensions. The adjustable arch curve provides a user with multiple adjustments of the parameters of the arch curve for therapeutic treatment of various foot conditions. The arch support brace is sized in right and left shaped arch braces to fit underneath either the right or left arch of the user's feet. The arch support brace is easily removable without adjusting the arch curve height for placement in any pair of foot wear.

The present invention further discloses a method of treatment of inflamation and pain in the foot by applying an arch support brace having an adjustable arch curve under the foot. The method includes selectively and periodically adjusting the height and slopes of the arch curve, by user manipulating of the tensioning and adjusting means attached under the arch curve. The method provides therapeutic support and strengthening of the user's arches to relieve inflamation and pain associated with plantar fasciitis and/or tendinitis of related connective tissues and joints of the foot.

BRIEF DESCRIPTION OF SEVERAL VIEWS OF THE DRAWINGS

The above mentioned features of the invention will become more clearly understood from the following detailed description of the invention contained herein, read together with the drawings in which:

FIG. 1 is a pictorial view of the arch support brace having a self-adjustable arch curvature of the present invention in an uncompressed configuration;

FIG. 2 is an enlarged partial sectioned view along lines 2—2 of FIG. 1 illustrating one embodiment of a mounting bracket of a tensioning means positioned underneath the self-adjustable arch curve;

FIG. 3 is a side view illustrating the medial longitudinal arch curve in an uncompressed configuration having a foot positioned on the arch support brace;

FIG. 4 is a partial side view illustrating the arch curve in a compressed configuration including one embodiment of a tensioning means;

FIG. 5 is a partial bottom view of one embodiment of a tensioning means having an adjustable length for adjusting the arch curvature;

FIG. 6 is a pictorial view illustrating an alternative embodiment of the arch support brace having a self-adjustable arch curve;

FIG. 7 is an enlarged partial sectioned view along lines 7—7 of FIG. 6 illustrating an alternative embodiment of a mounting bracket of a tensioning means positioned underneath the self-adjustable arch curve;

FIG. 8 is a partial side view of one embodiment of a tensioning means having an adjustable length with the arch curve in an uncompressed configuration;

FIG. 9 is a partial side view of one embodiment of a tensioning means having a shortened length with the arch curve in a compressed configuration;

FIG. 10 is an opposing side view of FIG. 3 of the arch support brace having an alternate orientation of angled cuts along the self-adjustable arch curve of the present invention;

DETAILED DESCRIPTION OF THE INVENTION

Figure 11:
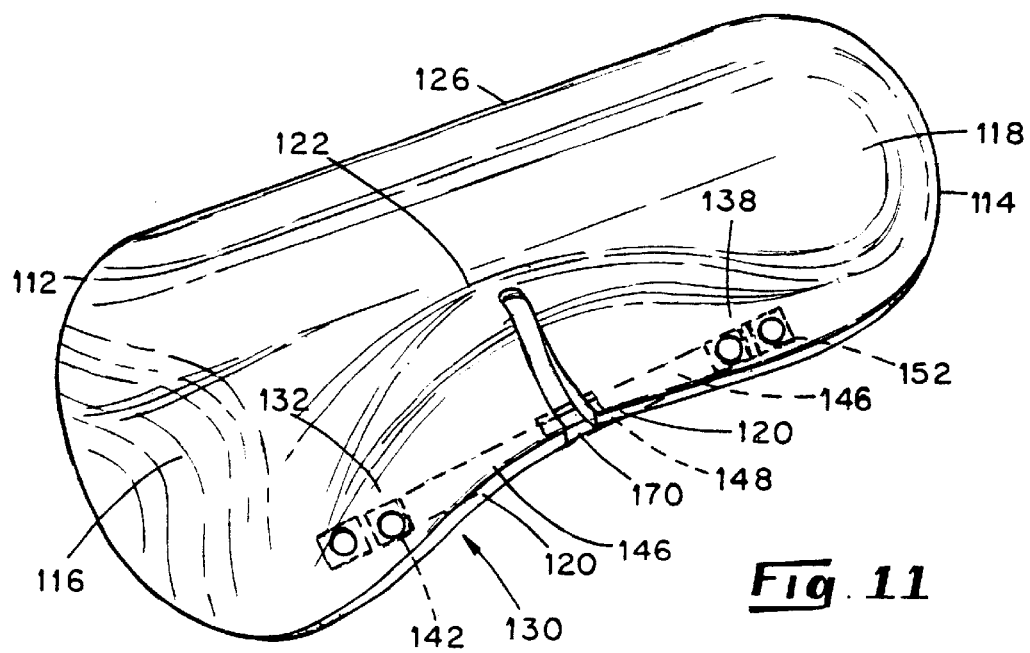
FIG. 11 is a pictorial view illustrating an alternative embodiment of the arch curve having one incision thereon.

An adjustable arch support brace and method of treating inflammation in the foot is disclosed incorporating various features of the present invention as illustrated generally for an arch support brace at 110 in FIGS. 1–10. The arch support brace includes a contoured orthotic platform sized to support the foot of a user from approximately the forefoot, or anterior 112 region, to about the heel, or posterior 114 region of the foot 190 of a user (see FIGS. 1 and 3). The anterior 112 region includes a transverse arch curvature 116 for support of the metatarsal bones of the forefoot (see FIG. 1 and 3). The posterior 114 region includes a concave heel section 118 for support of the calcaneus heel bone of the talus area of the foot 190 (see FIGS. 1 and 3).

The arch support brace 110 can be sized and shaped in various lengths, widths, and adjustable arch curve heights to accommodate users having a narrow, rigid foot with a high arch (pes cavus), a medium arch, or can be sized and shaped to accommodate users having a generally more flattened foot (pes planus). The arch support brace 110 is removably placed underneath the foot of a user, and placed upon a foot supporting surface such as under, or on top of, the insole of any appropriately sized shoe or sandal, or can replace the insole of a shoe or sandal. The arch support brace 110 is shaped as for support of the arch of a right foot or the arch of a left foot, and can be utilized as a pair of right and left arch support braces for simultaneous treatment of inflamation and pain in both user's feet. The arch support brace 110 is quickly removable and placed in any pair of foot wear by the user, including dress shoes, casual shoes, athletic shoes, ski boots, foot support casts, and/or in sandals, without disassembly of the arch support brace.

The arch support brace 110 includes an interior arch side 120 of the medial longitudinal arch curve 130 (hereinafter, arch curve) which includes an upper surface, and a central or medial arch slope 122 having a sloped portion extending toward the lengthwise axis or center midline 124. The arch curve 130 slopes downwards in a forward direction towards the transverse arch curvature 116, and slopes downwards in a rearward direction towards the concave heel section 118. The arch curve 130 also slopes laterally outwards towards an outer edge 126 (see FIG. 1). The lengthwise center midline 124 extends from the transverse arch curvature 116 to the concave heel section 118. On the outer side of the lengthwise central midline 124 is the outer edge 126 that is sloped slightly upwards along the outer perimeter of the arch support brace 110 for support of the outer portion of the foot 190. The underside 128 of the arch support brace 110 includes a curved portion 136 (see FIG. 3) that generally follows the arch curve 130 of the upper surface of the arch support brace 110.

Extending from the interior arch side 120, across to the central arch slope 122, is the upper surface of the arch curve 130 that includes a plurality of V-shaped or wedge cuts 170 (see FIGS. 1, 3 and 4). The plurality of cuts 170 provide for inherent self-adjusting of the arch curve 130 in height, slope, and curvature during application of varying forces F (see FIG. 4) imposed onto the arch support brace 110 by the user's foot 190 during standing, walking, jumping, and/or running motions by the user.

Each of the plurality of wedge cuts 170 is about 0.5 millimeter to about 1.0 millimeter wide at the smaller width proximate the center midline 124, and each wedge cut 170 extends to a wider opening width 180, 182 ranging from about 3.0 millimeter to about 10.0 millimeter width proximate the interior arch side 120. One embodiment of the arch support brace 110 includes a hole 178 of about 1.0 millimeter to about 3.0 millimeter in diameter oriented proximate the center midline 124 at the origination of each wedge cut 170, with each wedge cut beginning with a width of about 1.0 millimeter to about 2.0 millimeter at each hole 178, and each wedge cut extending to a wider opening width 180, 182 ranging from about 3.0 millimeter to about 10.0 millimeter along the interior arch side 120. Each cut 170 does not require the same opening width along the interior arch side 120, therefore the wedge cuts proximate the anterior slope 134 and the posterior slope 138 may have an opening width 180, 182 of about 3.0 millimeter to about 4.0 millimeter, while the middle wedge cuts 170 along the upper portion of the arch curve may have an opening width of about 2.0 millimeter to about 4.0 millimeter, or alternatively about 4.0 millimeter to about 10.0 millimeter. Alternatively, each wedge cut 170 may have a different opening width in the range of about 1.0 millimeter to about 10.0 millimeter.

Each wedge cut 170 is separated by a plurality of extensions 172 (see FIG. 1, which are maintained in a spaced apart configuration when not compressed by the forces F potentially placed onto the arch support brace 110 by a foot 190 (see FIGS. 3 and 4). As illustrated in FIG. 1 for one embodiment having four wedge cuts 170, each of the plurality of extensions 172 have an originating end 174 that is generally proximate the descending slope of the central arch slope 122. Each originating end 174 serves as a generally rigid base for a flexibly resilient cantilevered arm and end for each extension 172 that is determined by the length and width of each extension 172, and the composition and thickness of the arch support brace 110, along with the tension maintained on the arch curve 130. An example of the composition of the arch support brace 110 includes a high density, generally rigid, polyester plastic, an acrylic resin, a graphite reinforced polyester plastic, or a light-weight metal with a sufficient rigidity for adequate support of a user's weight. The arch support brace 110 may be designed with varying thicknesses along the length and width of the arch curve 130 to further add to the rigidity of each cantilevered extension 172 of the arch curve 130. With each originating end 174 and extension 172 serving as a cantilever, each weighted extension end 176 is moved downwards during compression by force F (see FIG. 4) to a weighted height of the arch curve 130. Each downwardly moved extension end 176 is returned to an unweighted or lesser weighted configuration (see FIGS. 1 and 3) by the resistance to bending of the substantially rigid base of each extension, in combination with the flexibly resilient cantilevered arm and end for each extension as determined by the composition and width of each originating end 174 and the length of each extension 172. After force F is diminished against the upper surface of the arch curve 130, the extensions 172 return inherently to an unweighted curvature and neutral height (see FIG. 3) for maximal support of the arch of a user's foot during sitting and/or reclining when the brace 110 is maintained against the user's foot.

As the user's foot 190 compresses the arch curve 130 (see FIGS. 3 and 4), the plurality of wedge shaped extensions 172 are compressed downwards, with each interior side of each compressed extension end 176 being positioned proximate but not directly touching an adjacent side of an extension end 176 (see FIG. 4). The user may apply excessive weight and force on the arch curve 130 during jumping or running that may exceed the designed rigidity of the materials composing the arch curve 130, therefore each respective adjacent side of each downwardly moved cantilevered extension end 176 may contact adjacent sides during a fully compressed moment of a foot-strike, therefore providing a lower height limit that the arch curve 130 maintains for support of the curve of the arch of the user's foot, thereby limiting continued tearing and stretching of the plantar fascia and/or other connective tissue within the foot during prolonged walking or vigorous physical exercise. The lower height limit for the arch curve 130 is partially dependent on the flexible resiliency of each cantilevered arm and end for each extension of the arch curve as determined by the composition of materials of the arch curve. An alternative arch curve may include reinforcing segments added to portions of the arch curve such as metallic segments, reinforced acrylic or polyester plastic segments, graphite filaments, or other combinations of rigid materials.

The lower height limit for the arch curve 130 and flexibility of each resilient cantilevered arm and end for each extension 172 is further determined by the combination of the width of the cuts, the length of the cuts, and any additional means of tensioning (see below) attached under the arch curve 130. An unweighted position, such as sitting, or a minimally weighted position, such as standing but leaning on the opposite foot, provides each extension 172 position (FIGS. 1 and 3) having a width of each cut opening 170 of between about 2.0 millimeter to about 5.0 millimeter, with a alternative range of between 1.0 millimeter to about 10.0 millimeter. Each extension 172 can be a different length extending from about the center midline 124 to the interior arch side 120 of the arch curve 130. Extensions 172 along the anterior slope 132 and the posterior slope 138 may be shorter in length than the extensions 172 that are oriented proximate the upper surface of the arch curve 130. In one embodiment illustrated in FIG. 1, each of the extensions 172 are approximately the same length as extended from the center midline 124. In an alternative embodiment illustrated in FIG. 6, each extension 272 is a different length and sized to extend along the anterior, medial, and posterior curvatures of arch curve 230 in a radiating pattern (see FIGS. 6 and 10).

The anterior slope 132 (see FIGS. 1 and 3) along the forward surface of the arch curve 130, includes an anterior angle 134 (see FIG. 3) that is adjustable in angle by manipulation of a means for tensioning 146 and a means for adjusting 148 (see FIGS. 3, 4, and 5) that are positioned underneath the arch curve 130. A posterior slope 138 includes a posterior angle 140 (see FIG. 3) that is adjustable in angle by manipulation of the means for tensioning 146 and means for adjusting 148 (see FIGS. 3, 4 and 5). One embodiment of the tensioning means is a connector such as a band 146 (see FIG. 5) that is flexible to allow bending flex in a vertical direction when the band 146 is not tightly tensioned, but is generally non-extensible along its linear length. The band 146 is composed of material known to those skilled in the art to provide a band that are non-extensible in length and is capable of supporting linear length stresses of up to about 200 pounds to about 300 pounds without stretching or breaking. Examples of materials for the band 146 include galvanized steel, stainless steel, other metal materials, or a composite plastic material having reinforcing filaments that are non-extensible in length. The band 146 is connectable at an anterior end 142 (see FIG. 1), underneath the anterior slope 132 by connectors 144, 144' inserted through openings 158, 158', and is connectable at a posterior end 152 (see FIG. 2), underneath the posterior slope 138 by connectors 154, 154' inserted through openings 160, 160'. The band 146 is preferably of a preselected length to fully extend from a forward position proximate the origination of the anterior slope 132, to a position proximate the origination of the posterior slope 138. The band 146 is interchangeable by removal and reconnecting of the respective connectors with a separate band of a lesser length, to provide a greater tension and higher neutral height of arch curve 130, or may be interchangeable with a longer length band to provide a lesser tension and a lesser neutral height of arch curve 130.

One embodiment of the means for tensioning 146 includes an adjustable length band 146 having a means of adjusting 148 positioned along the length of the band 146, for user adjustments of the horizontal length 164 of the band 146, thereby providing adjusting the tension on, and the neutral height of the arch curve 130, adjusting the anterior angle 134, and adjusting the posterior angle 140 for user adjustable support of the arch and angle of declination of the user's foot. The band 146 includes a first end portion 142 having a plurality of lateral oriented slots 156 along the center of the band, with the first end portion 142 attached to the means of adjusting 148. A second end portion 152 of the band, having a plurality of lateral oriented slots 156 along the center of the band, is positionable to fit into the means of adjusting 148 for drawing the second end portion toward the first end portion 142 A worm gear 148 is connectable on the first end portion 142, or alternatively, connectable on the second portion 152, with the other end portion of the band 146 being drawn into and through the worm gear 148 in a worm drive configuration known to those skilled in the art. An adjustment screw 150 fits into the worm gear 148, to allow adjusting of the horizontal length 164 of the band 146, by moving the first end portion 142 relative to the second end portion 152 by manipulating the adjustment screw 150 fitting into the worm gear 148, with the threads (not shown) of the adjustment screw contacting against the plurality of slots 156 of the second end portion 152, thereby adjusting the length of the first end portion 142 in relation to the second end portion 152, and adjusting the overall length of the ends of the band 146. The segmented band and worm gear provides the user with an adjusting means to self-adjust the overall length of the band 146, which draws the connectors 144, 144' toward or apart from connectors 154, 154', thereby adjusting the neutral or unweighted height of arch curve 130. The adjustment screw 150 is user adjustable within the worm gear 148 by a screwdriver, allen wrench, or other tool know to those skilled in the art.

Adjusting the worm gear 148 to lengthen the band 146 allows the arch curve 130 to have a lesser neutral or unweighted height than a prior arch height position, thereby providing less tension along the arch curve, and allowing each extension 172 to move downwards a distance as force F is placed on arch curve 130. Shortening the length of the band 146 forces the arch curve 130 to increase in neutral height while lifting each extension 172 of the arch curve 130, thereby providing more tension along the arch curve 130 and reducing the flexibility of each flexibly resilient cantilevered arm and end for each extension 172, therefore providing more support of the arch of a user's foot. Shortened band lengths also increase the anterior angle 134, and increase the posterior angle 140, therefore providing an increased posterior slope 138 to maintain a preferred angle of declination that the plantar fascia forms when properly attached to the calcaneus heel bone. The descending posterior slope 138 is preferably maintained at about a 14° angle to about a 16° angle by adjustment of the length of the band 146, to adequately support the calcaneus heel bone in a preferred position, and to support the arch curve of the user's foot, while protecting the plantar fascia attachment at the calcaneus bone.

An optimal therapeutic angle for the posterior angle 140 is about 15° for the descending posterior slope 138 of the arch curve 130 upper surface to maintain therapeutic support of the arch of the user's foot. The angle 140 of the descending posterior slope 138, when adjusted to the optimal therapeutic angle by the user's manipulation of the tensioning and adjusting means, provides support for the preferred orientation of the calcaneus heel bone in relation to the plantar fascia. The calcaneus heel bone's orientation with a generally flat foot supporting surface is referred in medical terminology as the angle of declination, the calcaneal angle of inclination, or alternately the angle that the plantar fascia forms when properly attached, without tearing, to the calcaneus heel bone. When the angle of declination decreases for a user's foot, as when the calcaneus bone rotates toward a more horizontal orientation during aging (called "falling arches"), there is a resulting partial tearing of the plantar fascia attachment at the calcaneus heel bone. The adjustable arch curve 130 is designed to allow a user, under the direction of a physician by written or verbal instructions, to periodically adjust the tensioning means to maintain the posterior angle 140 of the posterior slope 138 at about an angle optimal to support the user's arch in relation to the calcaneus bone in a preferred configuration. When the arch of the user's foot is properly supported, the plantar fascia is protected from tearing at the calcaneus bone, therefore reducing or eliminating the pain associated with plantar fasciitis or associated tendinitis in the feet. As a user periodically adjusts the arch curve neutral or unweighted height of the arch curve 130 for each arch support brace 110 worn, an optimal neutral height for support of each of the user's arch is attained, to provide the user with a method of constant support and strengthening of the arch of each foot during every segment of each stride taken by the user, and during sitting and relaxing, while wearing the arch support brace 130. As the user periodically adjusts the tensioning and adjusting means, the prior medical practice is eliminated of requiring repetitive visits to a physician for adjustment of the fit and replacement of a rigid orthotic made from a cast of the user's foot. The user is provided with an adjustable arch curve that fits properly for each arch support brace 110 worn, without repetitive visits and instructions from a physician such as a podiatrist who may initially prescribe the arch support brace 110, and may initially describe the method of treatment (disclosed herein below) utilizing the arch support brace 110 for therapeutic treatment of plantar fasciitis and related foot disorders. The treatment method may be minimally supervised by an attending physician, with self-monitoring by the user over a treatment period of a plurality of months and years for treatment of chronic plantar fasciitis and related foot disorders, and preventive maintenance treatment as the user's feet age and/or as the user modifies his or her daily routine and imposes different stresses on the feet by changes in working conditions and exercise habits.

An alternative embodiment for the band 146 utilized as a tensioning means includes dual parallel bands (not shown) that are attachable side-by-side under the arch curve, oriented lengthwise, attached between connectors at each band end positioned respectively under the anterior slope 132 and the posterior slope 138 of the arch curve 130. Each of the bands includes an adjusting means for separately adjusting the length of each band, to independently raise or lower the interior arching side 120 by adjusting the length of the first band, while applying a different tension to the arch curve under the center midline 124, by adjusting the length of the second band.

An alternative embodiment having at least one cut 170' along the arch curve 130 is illustrated in FIG. 11. In FIGS. 6–10, an alternative arch brace 210 having a plurality of angled wedge cuts 270, means for tensioning 242, 246, and means for adjusting 250 is illustrated. The plurality of wedge cuts 270 create a plurality of v-shaped extensions 272 (see FIG. 6). The wedge cuts 270 originate along the interior arch side 220 of the arch curve 230, and are radially angled outwards from the interior arch side toward the longitudinal center midline 224 of the arch curve 230, and toward the outer sloped edge 226 of the arch brace 210 (see FIG. 6). An alternative orientation of angled cuts 270' is shown in FIG. 10.

The interior end of each angled cut ends at a hole 278 is a hole 278 of about 1.0 millimeter to about 3.0 millimeter in diameter positioned proximate the center midline 224. At least one anterior cut is angled in orientation toward the anterior end 212, and at least one posterior cut is angled in orientation toward the posterior end 214. The interior ends of the middle, upper surface cuts are oriented radially along the curvature of the central arch slope 222 and are generally directed toward the center midline 224 of the arch brace. As illustrated in FIG. 6 for one embodiment having four wedge cuts 270, each of the plurality of extensions 272 have an originating end 274 that is generally wide in width along the respective slopes of the arch curve 230. Each originating end 274 serves as a cantilever having a substantially rigid base and having a flexibly resilient cantilevered arm and end for each extension 272 that is determined by the length and width of each extension 272, and by the composition and thickness of the arch curve 230, along with the tension maintained on the arch curve 230.

Regardless of the shape of the cuts and extensions, whether generally aligned incisions providing rectangular extensions 172 (see FIG. 1), or angled cuts 270 providing v-shaped extensions 272 (see FIG. 6), the sides of each extension are forced in close proximity to adjacent sides during each foot-strike by force being transferred by the foot 190 of the user onto the arch curve 230, thereby collapsing the neutral height of the arch curve 230 as the plurality of extensions 272 move downward and are forced into a lesser curvature having extensions ends 276 in a compressed position. Each interior side of each compressed extension end 276 is positioned proximate to, but is normally not directly touching, an adjacent side of an extension end 276 (see FIG. 9). The user may apply weight and excessive force on the arch curve 230 during jumping or running that may exceed the designed rigidity of the materials composing the extensions of the arch curve 230, therefore each respective adjacent side of each downwardly moved extension end 276 may contact adjacent sides during a fully compressed moment of a foot-strike. A lower height limit is provided for the arch curve 230 to maintain adequate support of the curve of the arch of the user's foot, thereby limiting continued tearing and stretching of the plantar fascia and/or other connective tissue within the user's foot during prolonged walking or vigorous physical exercise. The lower height limit for the arch curve 230 is partially dependent on the rigidity of the extensions of the arch curve, as determined by the composition of materials of the arch curve, and is dependent on the tension maintained on the arch curve by a tensioning and adjusting means. The underside 228 of the arch support brace 210 includes a curved portion 236 (see FIGS. 9 and 10) that generally follows the arch curve 230 of the upper surface of the arch support brace 210.

An alternative tensioning and adjusting means is positioned proximate the underside curved portion 236 of the arch curve 230. The tensioning means includes a first, generally non-extensible, length of cable 242 having an anterior end connectable to a connection bracket 244 to the underside of the leading portion of the anterior slope 232 with connectors known to those skilled in the art (see FIGS. 7 and 8), such as a screwable post or a rivet that includes an upper surface that can protrude through, and are generally flush with the upper surface of the arch curve 230. A second, generally non-extensible, length of cable 246 having a posterior end connectable to a connection bracket 252 to the underside of the posterior portion of the posterior slope 238 with connectors known to those skilled in the art (see FIGS. 7 and 8) that are generally flush with the upper surface of the arch curve 230. The lengths of cable 242, 246 can be composed of stranded wire, or stranded carbon-fiber filaments that are generally non-extensible in the length dimension, and are generally rigid but can be minimally bent to allow flexing of the cables in a vertical direction without breakage during high-force impacts of a foot on the arch support brace 210 such as during running and/or participation of the user in sports requiring jumping, sudden stopping and pivoting of the feet.

Each cable is attached to, or threaded into, respectively a connectors 262, 266 that attach into a adjusting means positioned generally at a mid-section underneath the underside portion 236 of the arch curve 230. The adjusting means can include a rotatable sleeve nut (not shown) or a turnbuckle 250 (see FIGS. 8 and 9). The turnbuckle 250 is generally known to those skilled in the art to be designed with a first, or anterior end, and a second, or posterior end, for attaching to a respective threaded end of two opposed, aligned cables 242, 246. The turnbuckle 250 provides an adjustment means that is rotatable to draw each respective cable 242, 246 together in length during tightening, or to extend apart in length during loosening. As user rotates turnbuckle 250 in one direction of rotation, the cables 242, 246 are shortened in overall length, with connectors 244, 252 drawn closer together, thereby increasing the anterior angle 234 of anterior slope 232, and increasing the posterior angle 240 of posterior slope 238, with resulting increase in the neutral height of the arch curve 230 during uncompressed configurations (see FIG. 8), and an increase in arch curve height during compressed (see FIG. 9) configurations of the arch curve 230. The height and slopes 232, 238 of the arch curve 230 can be reduced by the users manipulation of the turnbuckle 250 to extend cables 242, 246 apart in overall length. Therefore, the height and slope of arch curve 230 of the arch brace 210 is self-adjustable by the user, with advice from a physician, to provide for adjustable support of a "falling arch" to treat plantar fasciitis or related foot disorders. Further, a systematic method of therapeutic treatment of inflamation and pain of plantar fasciitis while supporting the arch is provided by periodically adjusting the neutral (unweighted) height and slopes of the arch curve 230 to support the user's arch in unweighted height and weighted height configurations with the adjustable arch brace 210, with resulting strengthening of the user's arch over a treatment period as determined by the user and/or an advising physician.

The inherently self-adjusting arch height feature of the adjustable arch support brace 110, 210 provides a therapeutic treatment method for sufferer's of plantar fasciitis or related tendinitis and painful foot disorders, by maintaining the preferred arch height, thereby preventing the arch from collapsing excessively with each foot-step for prevention of excessive stretching of the plantar fascia and related connectors of the user's foot. As the arch curve of each foot flattens during the aging process and during prolonged sporting activities, the generally stretched plantar fascia of each foot can be stretched excessively during running, tennis, and/or vigorous walking, with resulting partial tearing of the plantar fascia attachment at the calcaneus heel bone. As tearing progresses, the condition identified as plantar fasciitis occurs, with continued pain due to repetitive irritation and inflamation of the plantar fascia during each step by a user, whether walking or running. Once partial tearing and inflamation occurs of the plantar fascia, re-injury occurs frequently and as often as each morning as a sufferer takes his or her first steps after a night of relaxation and partial healing of the plantar fascia of each foot.

To remedy continued partial tearing and inflamation of the plantar fascia and/or related foot connector tissues, a method of treatment is disclosed that utilizes an adjustable arch support brace 110, 220 for applying against the user's arch curve, stabilizing the bone structures of the arch curve at a preferred height, and minimizing the stresses imposed by an unsupported arch on the plantar fascia attachment at the calcaneus heel bone. The arch support brace 110, 210 allows limited flex of the user's arch and increases comfort during wearing by providing a significant degree of user adjustments of arch curve height and slopes, while providing a generally rigid arch support at a weighted minimum arch height determined by a user or physician, thereby maintaining a minimum arch curve height for support of the user's arch by the user adjusting of the tensioning and adjusting means attachable to the underside 128, 228 of the arch support brace 110, 210.

A method of treatment of inflammation in the feet due to plantar fasciitis and related foot disorders is disclosed. During initial treatment, a physician or an advising person may measure significant angles of the foot, such as the angle of inclination, and/or the neutral height of the arch curve of each of the user's feet. The physician, other advisor, or the user selects an appropriately sized adjustable arch support brace 110, 210, adjusting the adjustable arch curve 130, 230 height and slopes by manipulating the tensioning and adjusting means to position the adjustable arch curve 130, 230 in a preferred orientation under the arch of a user's foot, therefore providing immediate support of either arch, or both arches of the user's feet. Alternatively, the user receives verbal or written advice for selecting a properly sized arch support brace 110, 210, along with directions for manipulating of the tensioning and adjusting means, thereby allowing the user to self-prescribe and obtain in the marketplace an adjustable arch curve 130, 230 for comfortable and therapeutic wearing of the arch support brace 110, 210.

The method includes selectively and periodically adjusting the height and slopes of the arch curve, by user manipulating of the tensioning and adjusting means attached under the arch curve, to increase or lessen the neutral height and tension on the arch curve for comfortable and generally rigid support of the user's foot. The method further includes readjusting at periodic time periods to an alternative weighted height, thereby adjusting the angle of the anterior slope, the angle of the posterior slope, and the height of the arch curve by user manipulating of the tensioning and adjusting means. The adjustable arch brace is removable and reinsertable in any shoe, boot, sandal, or foot support platform preferred by the user, therefore maintaining continuous treatment of the inflammation in the user's feet with any foot wear chosen by the user during sitting, walking, running, or any other forms of exercise.

The method of treatment of inflammation in the foot provides continuous therapeutic support and strengthening of the user's arches to relieve inflamation and pain associated with plantar fasciitis, tendinitis of related connective tissues, and/or inflammation of related joints of the foot. During preventive and/or maintenance steps of treatment, the adjustable arch curve 130 (or 230) height and slopes are increased or decreased by the user in proportion to the extent of inflammation as indicated by pain in the arch, metatarsal bones, and/or the calcaneus heel bone of the foot. The user can utilize the same arch brace, or a right and left pair of arch braces, with different adjustable arch curve 130 height and slope settings that are adjustable throughout a day or throughout a week depending on the walking and sitting activities of the user. Adjustments are conveniently made by the user of the arch curve 130 height and slope by remanipulating the tensioning and adjusting means before, during, and/or after sporting activities, thereby providing additional support during repetitive arch and foot impacts on the adjustable arch curve as imposed during strenuous sporting activities by the user. Due to the comfort provided by the adjustable arch curve 130, wearing of the arch support brace 110 may continue for numerous years as the user supports his or her feet with one or a pair of adjustable arch braces to minimize a recurrence of inflammation and pain in the user's arches and feet.

An alternative embodiment for the adjustable arch support brace includes an adjustable arch curve having an arch curve portion that is segmented and separated from an adjacent main portion of the arch brace. The segmented arch curve includes one or more v-shaped or rectangular shaped cuts originating at the interior arching side of the arch curve, therefore the arch curve is partially sectioned laterally across the width of the arch curve into two or more extensions that include uncut, bendable base portions of each extension that are connected to the arch curve. The segmented arch curve is connectable to the main portion of the arch brace by pliable straps or metal bands underneath the anterior slope, posterior slope, and medial portion of the segmented arch curve and corresponding anterior, posterior and medial portions of the arch brace. Alternatively, an elastic cover is utilized to cover the surfaces of the segmented arch curve and the arch brace to maintain the arch curve in proper orientation with the adjacent main portion of the arch brace. A height adjustment means is positioned underneath the segmented arch curve, including at least one gel pack or at least air bladder that are interchangeable with additional gel packs or air bladders having a greater or a lesser height. As weight from the arch of a user's foot is placed on, and off, the segmented arch curve, the height of the arch curve diminishes, and increases, in proportion to the firmness of the pliable gel pack or air bladder. The height of the segmented arch curve continuously changes in relation to the main portion of the arch brace by repetitive forces imparted during walking or running, with continuous support of the user's arch and foot provided to minimize damage while allowing treatment of plantar fasciitis and inflamation of related foot disorders.

An alternative embodiment includes an extended length adjustable arch brace extending from underneath the toes and phalanges bones, contoured in width to support the transverse arch, curved upwards to support the arch curve, and contoured in width across the heel of the foot. The extended length adjustable arch brace supports the metatarsals, the arch and associated plantar fascia, and the calcaneus bone of the heel.

Another alternative embodiment includes a self-adjustable arch support brace placed in or onto the upper surface of a sandal, with a generally thin, resilient cover over the upper surface of the arch support brace. The self-adjustable arch support brace provides therapeutic support for the arch of a foot that is partially enclosed by a sandal, without the need for a complete upper shoe enclosure as required by prior insole devices.

A further alternative embodiment includes an adjustable arch curve of an arch support brace having a tensioning and adjusting means, and further includes a curved band that is attachable at a plurality of positions underneath and following the arch curve. The curved band is attached at opposed band ends under the anterior slope and posterior slope of the arch curve. The curved band is further attached under each of the extensions of the segmented portion of the arch curve by about one connector for each extension, with each connector extending below the arch curve surface and through corresponding elongated slots in the curved band. The elongated slots allow adjusting movement of the curved band in relation to the extensions as the extensions are forced down in a weighted height position, or are resiliently rebound to an unweighted, neutral height position. The curved band is tensioned by an adjusting means such as a worm gear that forms a connection between two portions of the curved band. As the worm gear is adjusted, the curved band will extend in length, providing an upwards tension on the underside of each extension, to raise the height of the arch curve, and to provide increased resistance to downwards bending for each extension. As the curved band is reduced in length, a lesser tension is provided on the underside of each extension, lowering the height of the arch curve, and providing less resistance to decreases in height. An arch curve minimum height is controlled by the width of incisions between each extension, and further limited by the curved band rigidity in a horizontal dimension.

Figure 12:
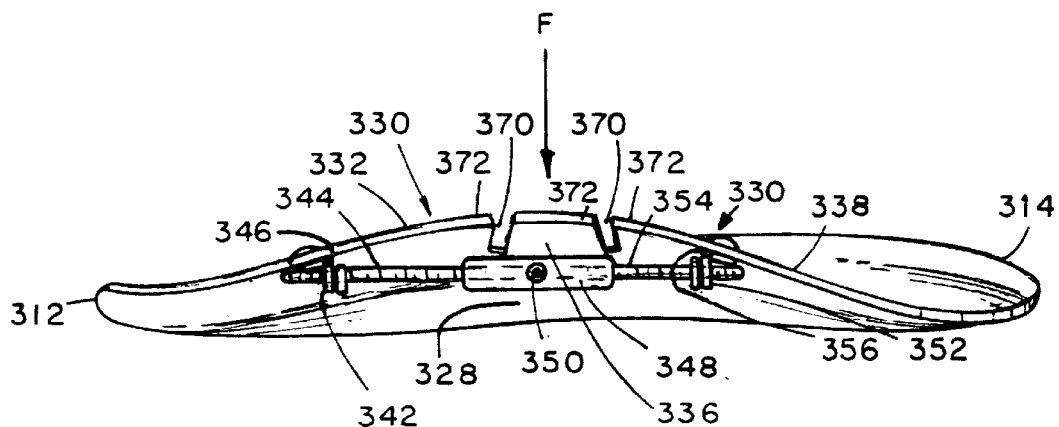
FIG. 12 is a pictorial view illustrating an alternative embodiment of a means for tensioning positioned under a self-adjustable arch curve.
Figure 13A:
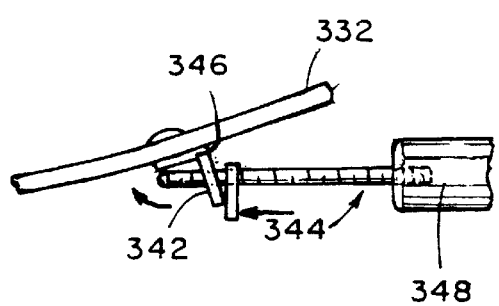
FIG. 13a is an enlarged partial side view of FIG. 12, illustrating an anterior slope connection of an alternative embodiment of a means for tensioning.
Figure 13B:
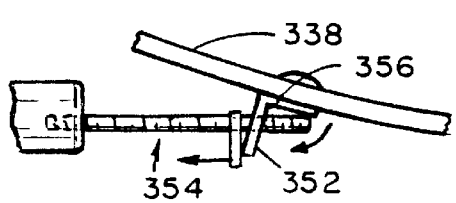
FIG. 13b is an enlarged partial side view of FIG. 12, illustrating a posterior slope connection of an alternative embodiment of a means for tensioning of the present invention.

A further alternative embodiment includes an adjustable arch curve 330 of an arch support brace having a tensioning means 348 and adjusting means 350, and includes at least two linkages 344, 354 connectable each by a pivoting bracket 346, 356 to, respectively, the anterior slope 332 portion and posterior slope 338 portion of the orthosis lower surface 336 (see FIG. 12). Each pivoting linkages 344, 354 may be elongated, "L" shaped, and aligned parallel to the orthosis lengthwise midline, with the tensioning means 348 and adjusting means 350 attached between each linkage. Each linkage may include a wing portion 342, 352 that is attached under, respectively, the anterior slope 332 and posterior slope 338 of the adjustable arch curve 330 having a plurality of extensions 372 separated by a plurality of incisions 370 along the arch curve 330. When the adjusting means 350 is manipulated to lengthen (see FIG. 13a) the distance between the anterior and posterior linkages 344, 354, each anterior and posterior wing portion 342, 352 is pivoted, respectively, toward the orthosis anterior end 312 and posterior end 314, thereby lowering the adjustable arch curve height. When the distance is shortened (see FIG. 13b) between the anterior and posterior linkages 344, 354, each anterior and posterior wing portions 342, 352 are pivoted, respectively, toward the arch curve 330 midportion 328 (see FIG. 12), thereby raising the arch curve 330 height, and increasing the anterior slope 332 and posterior slope 338 angles. An arch curve 330 minimum height is controlled by the width of the incisions 370 between each extension 372, and further limited by the resistance of each "L" shaped linkage from bending.

The self-adjustable arch support brace can also include a fastening mechanism on the underside surface of the arch brace such as a velcro or an adhesive material to position the arch curve properly in each shoe, and underneath the arch of the foot, and to allow the arch curve to be removably placed in any pair of shoes that the user wears without disassembly of the arch support brace.

Those skilled in the art will recognize the disclosure herein provides an improved adjustable arch brace including an adjustable medial longitudinal arch curve for therapeutic support of the arch of the foot at a preferred arch curve height during walking and running, and provides therapeutic treatment of heel spurs, plantar fasciitis, arch pain, tendinitis about the tarsus osseus, metatarsalgia, and/or related foot disorders.

The prior arch supports were composed of flexible materials such as leather, or rigid materials such as plastic, that were not adjustable in arch curve height and arch curvature without insertion of additional pads of foam, flexible materials, or heating and bending of rigid plastic materials to increase the arch height. In addition, prior applications of arch supporting members required a special boot that was not transferrable between shoes, and was not adjustable in arch height and slope during each stride.

While a preferred embodiment is shown and described, it will be understood that it is not intended to limit the disclosure, but rather it is intended to cover all modifications and alternate apparatus and methods falling within the spirit and the scope of the invention as defined in the appended claims.

What is claimed is:

1. An arch support brace having an adjustable arch curve, said arch support brace being fittable proximately under a foot and being sized and shaped to be removably placed within a foot support enclosure worn by a user, said arch support brace comprising:

an orthosis being sized for support of the underside of the foot, said orthosis including an upper surface having a forefoot portion, a heel portion, an interior side, a lengthwise midline, an outer lateral side, and a lower surface;

an arch support curve of said upper surface of said orthosis, said arch support curve having a medial longitudinal arch surface being curved upwardly along said orthosis interior side, said medial longitudinal arch surface including:

an anterior slope being inclined from said medial longitudinal arch surface toward said forefoot portion of said orthosis;

a posterior slope being inclined from said medial longitudinal arch surface toward said heel portion of said orthosis; and a medial slope being inclined from said interior side toward said outer lateral side of said orthosis; and an incision in said arch support curve along said medial longitudinal arch surface, said incision being originated along said orthosis interior side and being extended along said longitudinal arch surface, said arch support curve being maintained at a neutral height when in an unweighted position, said arch support curve having an interior end being disposed in an arched curve along a length dimension of said interior side of said orthosis;

whereby said arch support curve having said incision thereon is forced downwardly to a weighted position by the weight from the arch of the user's foot placed proximately upon said upper surface of said orthosis, said arch support curve having said incision thereon being flexibly rebounded to said neutral height when the weight from the arch of the user's foot is transferred off of said orthosis, thereby the arch of the user's foot is supported during use of said orthosis.

2. The arch support brace of claim 1, said arch support curve having said incision including:

a section along said medial longitudinal arch surface, said section being separated by said incision along said medial longitudinal arch surface, said incision being originated along said orthosis interior side and being extended along said medial slope, said section of said arch support curve being maintained at said neutral height along said arch support curve when in said unweighted position;

whereby said section of said arch support curve is forced downwardly during each user foot-strike proximately upon said upper surface of said orthosis, said section of said arch support curve moved to a weighted height along said arch support curve reduced below said neutral height, said section of said arch support curve flexibly rebounded to said neutral height when the user's weight is transferred off of said orthosis between each user foot-strike thereby the arch of the user's foot is supported during foot-strike and when unweighted.

3. The arch support brace of claim 2, wherein said arch support brace is sized for support of the foot from said forefoot portion of said orthosis proximate the metatarsal bones of the foot, to said heel portion of said orthosis proximate the calcaneus bone of the foot, said upper surface being contoured for support of the user's foot, said lower surface of said arch support brace being placed proximate a supporting surface of the foot support enclosure worn by the user, said arch support brace being removably placed without disassembly within any foot support enclosure worn by the user.

4. The arch support brace of claim 2, wherein said orthosis including a means for tensioning removably connectable between said anterior slope and under said posterior slope of said arch support curve, said tensioning means includes:

a band being generally rigid and having an anterior end and a posterior end;

at least two connectors connectable respectively at said anterior end and at said posterior end of said band, said anterior end connector attachable to said lower surface proximate said anterior slope, and said posterior end connector attachable to said lower surface proximate said posterior slope; and a means of adjustment of the length of said band, said adjustment means being connectable at about a mid-portion of said band, said adjustment means having a rotatable adjustment to decrease or increase the length between said anterior end and said posterior end of said band;

whereby when the length between said anterior end and said posterior end is decreased by the user adjustment of said adjustment means, the height of said arch support curve is increased, and said anterior slope and said posterior slope is increased, and when the length between said anterior end and said posterior end is increased by the user adjustment of said adjustment means, the height of said arch support curve is decreased, and said anterior slope and said posterior slope is decreased of said arch support curve.

5. The arch support brace of claim 4, wherein said band is segmented at about said mid-portion of said band into an anterior portion and a posterior portion of said band, said adjustment means including a worm gear connectable at said mid-portion of said band, thereby said anterior portion and said posterior portion connectable together by said worm gear, said rotatable adjustment including a rotatable screw fittable into said worm gear, whereby rotation of said rotatable screw either decreases or increases the length between said anterior end, and said posterior end of said band, whereby said height and slopes of said arch support curve are adjustable by the user.

6. The arch support brace of claim 2, wherein said wherein said incision includes a v-shaped incision being originated along said interior side of said orthosis, said v-shaped incision being extended along said medial slope.

7. The arch support brace of claim 2, wherein said incision includes an angled incision extended radially from said interior side of said orthosis, said radially angled incision being extended along said medial slope.

8. A foot support orthosis including an arch support brace having an arch curvature being self-adjustable during use, the foot support orthosis being fittable underneath the foot and being sized and shaped to be removably placed proximal a foot supporting surface of a shoe, a sandal, and/or a boot covering the foot of a user, the foot support orthosis comprising:

an orthosis being sized for support of the foot from underneath about the metatarsal bones of the foot, to underneath about the calcaneus bone of the foot, said orthosis having a first surface being contoured for support of the foot, having a second surface being downwardly faced for contact with the foot supporting surface of the shoe, and having a medial side and a lateral side on opposed sides of a central longitudinal axis of said orthosis;

a forefoot portion of said first surface being arcuately shaped to be positionable underneath the metatarsal bones of the foot;

a heel portion of said first surface being arcuately shaped to be positionable underneath the calcaneus bone of the foot;

a medial longitudinal arch curve proximate said medial side of said orthosis, said medial longitudinal arch curve being shaped to be positionable underneath the arch of the foot, said medial longitudinal arch curve having an upper surface being curved upwardly, said medial longitudinal arch curve including:

an anterior slope being inclined from said upper surface of said medial longitudinal arch curve toward said forefoot portion of said orthosis;

a posterior slope being inclined from said upper surface of said medial longitudinal arch curve toward said heel portion of said orthosis; and a medial slope being inclined from said upper surface of said medial longitudinal arch curve toward said lateral side of said orthosis; and said medial longitudinal arch curve being sectioned by one incision along said medial longitudinal arch curve, said sectioned medial longitudinal arch curve having said medial side being disposed in an arched curve along a length dimension of said medial side, said one incision being originated along said medial side of said medial longitudinal arch curve of said orthosis, said one incision being extended a pre-selected distance along said medial longitudinal arch curve;

whereby said sectioned medial longitudinal arch curve having one incision therein being forced to a weighted position during each foot-strike by force being transferred by the foot of the user from said heel portion and onto said medial longitudinal arch curve of said orthosis, thereby collapsing the height of said medial longitudinal arch curve, with each of said plurality of extensions flexibly rebounded to an unweighted position by force being transferred by the foot of the user from said medial longitudinal arch curve and onto said forefoot portion of said orthosis during each foot-strike by the user while wearing said orthosis.

9. The foot support orthosis of claim 8, wherein said medial longitudinal arch curve further comprises an underside surface having a curvature being generally parallel to said medial longitudinal arch curve curvature of said upper surface, said underside surface including:

an anterior bracket attachable to said underside surface at about said anterior slope, said anterior bracket having a wing portion positioned to extend downwardly from said underside surface under said anterior slope;

a posterior bracket attachable to said underside surface at about said posterior slope, said posterior bracket having a wing portion positioned to extend downwardly from said underside surface under said posterior slope;

a means for tensioning positioned between said anterior bracket and said posterior bracket, said means for tensioning including an anterior linkage aligned with said anterior bracket and a posterior linkage aligned with said posterior bracket, each of said anterior linkage and said posterior linkage is retractably extendable from respective opposed ends of said means for tensioning, each of said anterior and posterior linkage having a distal end being shaped to engage said respective wing portion of said anterior bracket and said posterior bracket, thereby each respective anterior and posterior bracket pivots respectively against said underside of said anterior slope and said posterior slope to change the height of said medial longitudinal arch curve; and a means for adjusting a length between each of said distal end of said anterior linkage and said posterior linkage of said means for tensioning, said means for adjusting being manipulated by the user;

whereby when each of said anterior linkage and said posterior linkage is extended from said means for tensioning by manipulation of said means for adjusting, the length between said respective distal ends is lengthened, thereby each distal end extends against said respective wing portion of said anterior bracket and said posterior bracket which pivot against said respective underside of said anterior slope and said posterior slope, thereby lowering the height of said medial longitudinal arch curve;

whereby when each of said anterior linkage and said posterior linkage is retracted toward said means for tensioning by manipulation of said means for adjusting, the length between said respective distal ends is shortened, thereby each distal end retracts from being against said respective wing portion of said anterior bracket and said posterior bracket which pivot toward said means for tensioning, thereby raising the height of said medial longitudinal arch curve height.

10. A foot support orthosis including an arch support brace having an arch curvature being self-adjustable during use, the foot support orthosis being fittable underneath the foot and being sized and shaped to be removably placed proximal a foot supporting surface of a shoe, a sandal, and/or a boot covering the foot of a user, the foot support orthosis comprising:

an orthosis being sized for support of the foot from underneath about the metatarsal bones of the foot, to underneath about the calcaneus bone of the foot, said orthosis having a first surface being contoured for support of the foot, having a second surface being downwardly faced for contact with the foot supporting surface of the shoe, and having a medial side and a lateral side on opposed sides of a central longitudinal axis of said orthosis;

a forefoot portion of said first surface of said orthosis being arcuately shaped to be positionable underneath the metatarsal bones of the foot;

a heel portion of said first surface of said orthosis being arcuately shaped to be positionable underneath the calcaneus bone of the foot;

a medial longitudinal arch curve having an upper surface being curved upwardly, said medial longitudinal arch curve including:
  an anterior slope being inclined from said upper surface of said medial longitudinal arch curve toward said forefoot portion of said orthosis;
  a posterior slope being inclined from said upper surface of said medial longitudinal arch curve toward said heel portion of said orthosis; and
  a medial slope being inclined from said upper surface of said medial longitudinal arch curve toward said lateral side of said orthosis; and one incision along said medial longitudinal arch curve, said medial side of said medial longitudinal arch curve being disposed in an arched curve along a length dimension of said medial side, said one incision including being originated along said medial side of said medial longitudinal arch curve of said orthosis, said one incision being extended a pre-selected distance along said medial longitudinal arch curve;

whereby said medial longitudinal arch curve having one incision thereon being forced together during each foot-strike by force being transferred by the foot of the user from said heel portion and onto said medial longitudinal arch curve of said orthosis, thereby collapsing the height of said medial longitudinal arch curve, with said medial longitudinal arch curve flexibly rebounded to an unweighted position by force being transferred by the foot of the user from said medial longitudinal arch curve and onto said forefoot portion of said orthosis during each foot-strike by the user while wearing said orthosis; and a means for tensioning said medial longitudinal arch curve connectable between an underside portion of said anterior slope and an underside portion of said posterior slope, said means for tensioning having a means for adjusting including a rotatable connector for user adjustment of a length of said means for tensioning connectable between said anterior slope and said posterior slope, whereby when the length of said means for tensioning is decreased by the user adjustment of said means for adjusting, the height of said medial longitudinal arch curve is increased, and each slope of said anterior slope and said posterior slope is increased, and when the length of said means for tensioning is increased by the user adjustment of said means for adjusting, the height of said medial longitudinal arch curve is decreased, and each slope of said anterior slope and said posterior slope is decreased.

11. A foot support orthosis including an arch support brace having an arch curvature being self-adjustable during use, the foot support orthosis being fittable underneath the foot and being sized and shaped to be removably placed proximal a foot supporting surface of a shoe, a sandal, and/or a boot covering the foot of a user, the foot support orthosis comprising:

an orthosis being sized for support of the foot from underneath about the metatarsal bones of the foot, to underneath about the calcaneus bone of the foot, said orthosis having a first surface being contoured for support of the foot, having a second surface being downwardly faced for contact with the foot supporting surface of the shoe, and having a medial side and a lateral side on opposed sides of a central longitudinal axis of said orthosis;

a forefoot portion of said first surface of said orthosis being arcuately shaped to be positionable underneath the metatarsal bones of the foot;

a heel portion of said first surface of said orthosis being arcuately shaped to be positionable underneath the calcaneus bone of the foot;

a medial longitudinal arch curve having an upper surface being curved upwardly, said medial longitudinal arch curve including:
  an anterior slope being inclined from said upper surface of said medial longitudinal arch curve toward said forefoot portion of said orthosis;
  a posterior slope being inclined from said upper surface of said medial longitudinal arch curve toward said heel portion of said orthosis; and
  a medial slope being inclined from said upper surface of said medial longitudinal arch curve toward said lateral side of said orthosis; and at least one incision along said medial longitudinal arch curve, said medial side of said medial longitudinal arch curve being disposed in an arched curve along a length dimension of said medial side, said at least one incision including being originated along said medial side of said medial longitudinal arch curve of said orthosis, said at least one incision being extended a pre-selected distance along said medial longitudinal arch curve;

whereby said medial longitudinal arch curve having said at least one incision thereon being forced together during each foot-strike by force being transferred by the foot of the user from said heel portion and onto said medial longitudinal arch curve of said orthosis, thereby collapsing the height of said medial longitudinal arch curve, with said medial longitudinal arch curve flexibly rebounded to an unweighted position by force being transferred by the foot of the user from said medial longitudinal arch curve and onto said forefoot portion of said orthosis during each foot-strike by the user while wearing said orthosis; and a means for tensioning said medial longitudinal arch curve connectable between an underside portion of said anterior slope and an underside portion of said posterior slope, said means for tensioning having a means for adjusting including a rotatable turnbuckle for user adjustment of a length of said means for tensioning connectable between said anterior slope and said posterior slope, whereby when the length of said means for tensioning is decreased by the user adjustment of said means for adjusting, the height of said medial longitudinal arch curve is increased, and each slope of said anterior slope and said posterior slope is increased, and when the length of said means for tensioning is increased by the user adjustment of said means for adjusting, the height of said medial longitudinal arch curve is decreased, and each slope of said anterior slope and said posterior slope is decreased.

* * * * *